(12) United States Patent
Tralshawala et al.

(10) Patent No.: US 7,549,789 B2
(45) Date of Patent: Jun. 23, 2009

(54) METHOD AND APPARATUS FOR THERMOGRAPHIC NONDESTRUCTIVE EVALUATION OF AN OBJECT

(75) Inventors: Nilesh Tralshawala, Rexford, NY (US); Donald Robert Howard, Troy, NY (US); Harry Israel Ringermacher, Delanson, NY (US); Bryon Edward Knight, Charlton, NY (US)

(73) Assignee: General Electric Company, Niskayuna, NY (US)

( * ) Notice: Subject to any disclaimer, the term of this patent is extended or adjusted under 35 U.S.C. 154(b) by 218 days.

(21) Appl. No.: 11/765,470

(22) Filed: Jun. 20, 2007

(65) Prior Publication Data

US 2008/0317090 A1 Dec. 25, 2008

(51) Int. Cl.
G01N 25/72 (2006.01)
(52) U.S. Cl. .................. 374/43; 250/341.6
(58) Field of Classification Search .......... 374/7, 374/43; 250/341.6, 330
See application file for complete search history.

(56) References Cited

U.S. PATENT DOCUMENTS

| | | | |
|---|---|---|---|
| 4,928,254 A * | 5/1990 | Knudsen et al. | 702/136 |
| 5,073,433 A * | 12/1991 | Taylor | 428/134 |
| 5,376,793 A | 12/1994 | Lesniak | |
| 5,564,830 A * | 10/1996 | Bobel et al. | 374/126 |
| 5,711,603 A | 1/1998 | Ringermacher et al. | |
| 6,367,968 B1 | 4/2002 | Ringermacher et al. | |
| 6,367,969 B1 | 4/2002 | Ringermacher et al. | |
| 6,394,646 B1 | 5/2002 | Ringermacher et al. | |
| 6,517,238 B2 | 2/2003 | Sun et al. | |
| 6,542,849 B2 | 4/2003 | Sun | |
| 7,409,313 B2 * | 8/2008 | Ringermacher et al. | 702/172 |
| 2005/0207468 A1 | 9/2005 | McCullough et al. | |
| 2007/0143061 A1 | 6/2007 | Ringermacher et al. | |

FOREIGN PATENT DOCUMENTS

EP 0089760 8/2007

OTHER PUBLICATIONS

Ringermacher, H.I., Howard, D.R., and Gilmore, R.S., "Discriminating Porosity in Composites using Thermal Depth Imaging", CP615, Review of Quantitative Nondestructive Evaluation vol. 21, ed, by D, O, Thompson and D, E. Chimenti, 2002, p. 528-535.

Harry Israel Ringermacher et al.; "Method and Apparatus for Thermographic Nondestructive Evaluation of an Object"; Pending U.S. Appl. No. 11/639,724, filed on Dec. 15, 2006.

(Continued)

*Primary Examiner*—Andre J Allen
(74) *Attorney, Agent, or Firm*—Penny A. Clarke

(57) ABSTRACT

A method and system for determining thermal diffusivity and porosity of an article are provided. The method comprises heating a surface of the article, capturing image data corresponding to an evolution of lateral heat flow from the surface of the article, applying a thermal time of flight analysis on the image data and determining thermal diffusivity and porosity values of the article using the thermal time of flight analysis for the lateral heat flow.

21 Claims, 4 Drawing Sheets

OTHER PUBLICATIONS

H. I. Ringermacher et al., "Systems and method for locating failure events in samples under load," U.S. Appl. No. 11/592,549, filed Nov. 3, 2006.

W. J. Parker et al., "Flash Method of Determining Thermal Diffusivity, Heat Capacity, and Thermal Conductivity," Journal of Applied Physics, vol. 32, No. 9, Sep. 1961, pp. 1679-1684.

H.I. Ringermacher et al., "Towards a Flat-Bottom Hole Standard for Thermal Imaging," Review of Progress in Quantitative Nanodestructive Evaluation, vol. 17A, 1998, pp. 425-429.

Z. Ouyang et al., "Thermal wave reflections of a pulsed stripe heat source from a plane boundary," Journal of Applied Physics, vol. 87, No. 8, Apr. 15, 2000, pp. 3999-4004.

C.S. Welch et al., "Remote measurement of in-plane diffusivity components in plates," Journal of Applied Physics, vol. 51, No. 3, Feb. 1, 1987, pp. 895-898.

B. Knight et al., "Advances in Thermal time-of-flight Imaging with Flash Quenching," Technical Information Series, 2006GRC146, Mar. 2006, Nondestructive Technologies Laboratory, Niskayuna, New York, pp. 1-7.

J.N. Zalameda et al., "Thermal Diffusivity Measurements on Composite Porosity Samples," Review of Progress in QNDE, vol. 9B, 1990, p. 1542.

P.H. Johnson et al., "Thermal and Ultrasonic Evaluation of Porosity in Composite Laminates," Review of Progress in QNDE, vol. 11B, 1992, p. 1555.

H. I. Ringermacher et al., "Synthetic Thermal time-of-Flight (STTOF) Depth Imaging," Review of Progress in Quantitative Nondestructive Evaluation, vol. 20, 2001, pp. 487-491.

* cited by examiner

METHOD AND APPARATUS FOR THERMOGRAPHIC NONDESTRUCTIVE EVALUATION OF AN OBJECT

BACKGROUND

The invention relates generally to nondestructive inspection techniques, and more particularly, to a thermographic nondestructive testing technique for determining flaws in an object.

Over the years, various nondestructive ultrasonic measurement techniques have been utilized to determine cross-sectional thickness of cast metal and other solid objects. Conventionally, the object is probed with ultrasonic waves, which penetrate the surface and are reflected internally at the opposite side or surface of the object. Based upon the time required to receive a reflected wave, the distance to the opposite (back) side can be determined, giving the thickness of the object at that point. Unfortunately, conducting ultrasonic measurements of this sort to examine the cross-sectional thickness would usually necessitate a cumbersome and time-consuming mechanical scanning of the entire surface with a transducer. In addition, to facilitate intimate sonic contact between the transducer and the object surface, a stream of liquid couplant must be applied to the surface or, alternatively, total immersion of the object in the couplant must be accommodated. Such accommodations, however, are most often not very practical or even feasible for numerous structural and material reasons. For example, ultrasonic systems capable of scanning and analyzing geometrically complex parts are typically very expensive and complicated. In addition, a mechanical scanning of the transducer over the surface of a large object can require substantial time delays, often of several hours.

In contrast, infrared (IR) transient thermography is a somewhat more versatile nondestructive testing technique that relies upon temporal measurements of heat transference through an object to provide information concerning the structure and integrity of the object. Because heat flow through an object is substantially unaffected by the microstructure and the single-crystal orientations of the material of the object, an infrared transient thermography analysis is essentially free of the limitations this creates for ultrasonic measurements. In contrast to most ultrasonic techniques, a transient thermographic analysis approach is not significantly hampered by the size, contour or shape of the object being tested and, moreover, can be accomplished ten to one hundred times faster than most conventional ultrasonic methods if testing objects of large surface area.

Conventionally, an infrared (IR) video camera has been used to record and store successive thermal images (frames) of an object surface after heating. Each video image is composed of a fixed number of pixels. In this context, a pixel is a small picture element in an image array or frame, which corresponds to a rectangular area, called a resolution element, on the surface of the object being imaged. Because the temperature at each resolution element is directly related to the intensity of the corresponding pixel, temperature changes at each resolution element on the object surface can be analyzed in terms of changes in pixel contrast.

One application of transient thermography is for non-contact quantification of porosity, voids, and delaminations in thin-walled carbon fiber reinforced polymer composite aircraft structures. Determining porosity using thermography is based on the calculation of thermal diffusivity, which in turn requires thickness information. In all known contemporary techniques, a calibrated reference standard for thickness is required or temperature dependent images are required to be generated, which may intrinsically have greater error than required for accurate analysis.

Further, to determine all diffusivity components in one measurement, such as in case of anisotropic materials, various heat flow methods have been proposed that require full parametric fitting of spatio-temporal temperature data. The measured values of spatial temperature profiles can become unreliable when surface emissivity is not uniform or when surface reflections from nearby hot or cold objects are in the IR camera field-of-view.

A quantitative time of flight (tof) infrared thermography technique based on determination of the "inflection point" has been disclosed in commonly assigned U.S. patent Ser. No. 11/639,724, Ringermacher et al., "Method and apparatus for thermographic nondestructive evaluation of an object," that obviates some of the aforementioned issues and provides diffusivity and thickness values.

However, there is a need for methods to determine diffusivity and porosity for composite articles that do not require exact thickness information, are not affected by surface emissivity variations or reflections, and do not require any sort of curve fitting to time-temperature data.

BRIEF DESCRIPTION

According to one embodiment a method for determining porosity of an article is provided. The method includes heating a surface of the article; capturing image data corresponding to an evolution of lateral heat flow from the surface of the article; applying a thermal time of flight analysis on the image data; and determining thermal diffusivity and porosity values of the article using the thermal time of flight analysis for the lateral heat flow.

According to another embodiment a non-destructive evaluation system for inspecting an object is provided. The system includes a heat source configured for heating a surface of the object, a focal plane array camera configured to capture a plurality of images corresponding to an evolution of lateral heat flow from the surface, an image acquisition system configured for capturing data corresponding to the plurality of images from the focal plane array camera, and a time of flight analysis system configured to perform a thermal time of flight analysis on the data, and determine diffusivity and porosity values using the thermal time of flight analysis for the lateral heat flow in the object.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The different embodiments described herein relate to non-destructive testing methods and systems for determining diffusivity and porosity values in an object using either high-speed IR transient thermography or alternatively using IR thermography with a steady step-heat source, particularly using the lateral heat flow principle.

Figure 1:
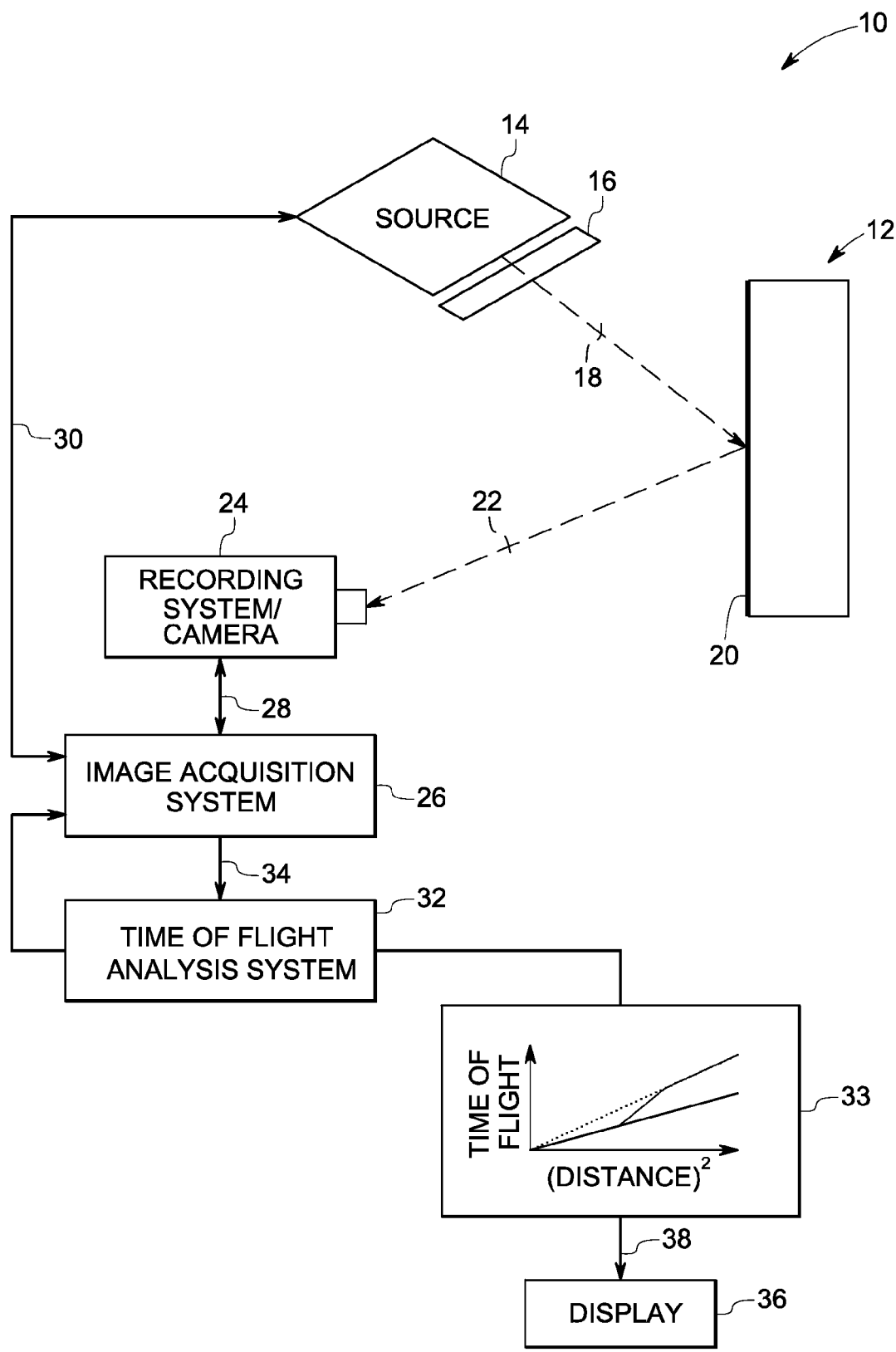
FIG. 1 is a diagrammatic representation of a non-destructive evaluation system for detecting diffusivity and porosity values in an object.

FIG. 1 shows a diagrammatic representation of a non-destructive evaluation system 10 for inspecting or for detecting flaws in a part or an object 12. The object 12 may be an industrial part, for example, a blade (turbine blade), a vane made of ceramics, combustion liner, a shroud or a similar part, for example for turbines or aircraft components. In one, non-limiting example, the object 12 is a composite article, for example an article made from anisotropic carbon fiber reinforced polymer (CFRP) composites.

Figure 2:
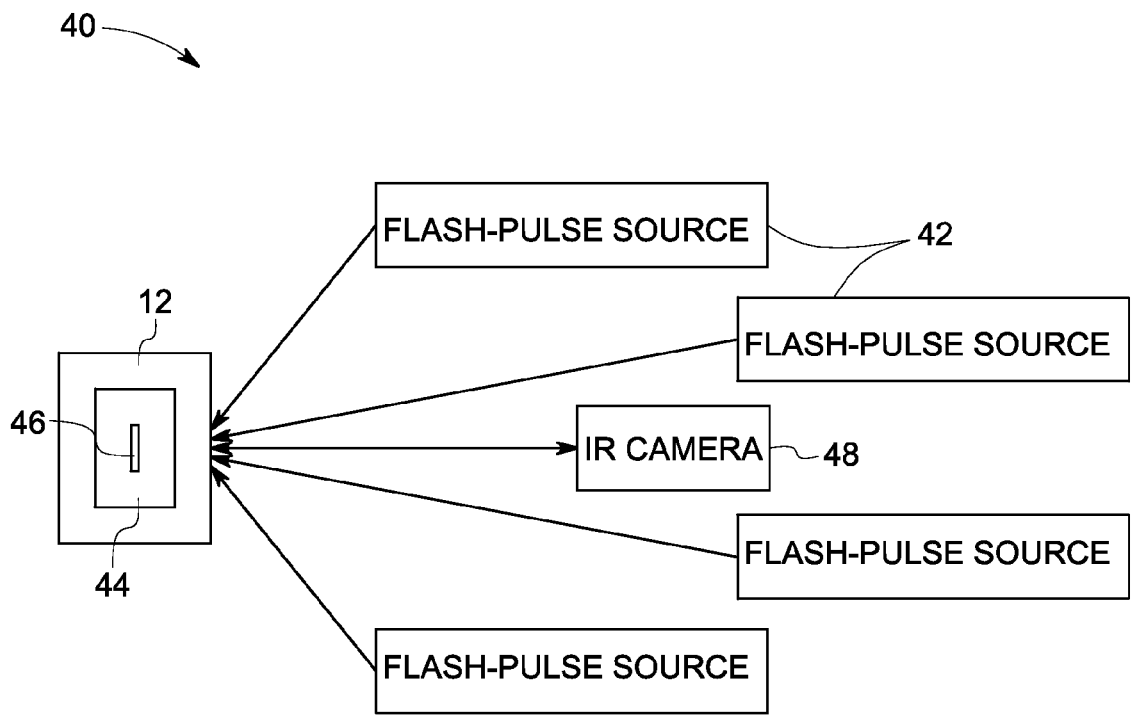
FIG. 2 is a diagrammatic representation of an exemplary embodiment of a non-destructive evaluation system with a flash-pulse heat source.
Figure 3:
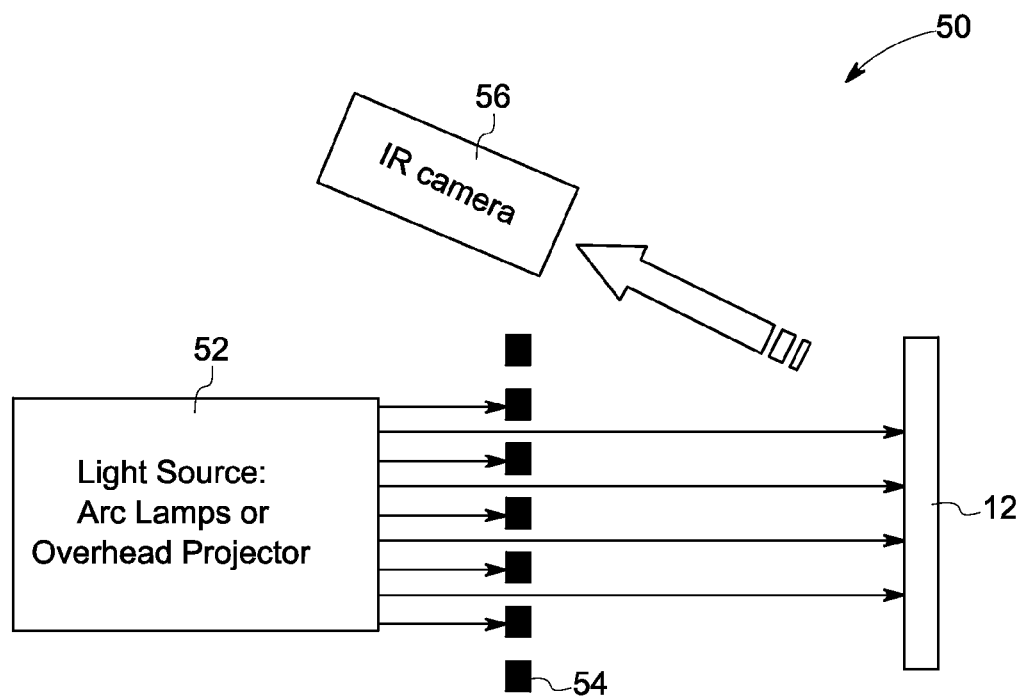
FIG. 3 is a diagrammatic representation of an exemplary embodiment of a non-destructive evaluation system with a step-heat source.

The system 10 includes a heat source 14 (for example, but not limited to a flash lamp or an overhead projector) for heating (heat applied is shown generally by reference numeral 18) optionally via a mask or a shutter 16, a surface 20 (or one side) of the object 12. Conventional thermal heat flow methods use a short, intense light pulse to uniformly heat one surface of a specimen before monitoring time evolution of either the front or the back surface temperature using an infrared (IR) camera. Such techniques are generally referred to as "flash IR" techniques. In one embodiment where the back surface temperature is monitored, the technique is called through-transmission (TT) thermography. In another embodiment where the same technique is used to obtain similar data from the front surface, the method is called single sided (SS) thermography, since both the source and infrared (IR) camera are on the same side. Apart from the flash IR methods, in another embodiment, time resolved infrared radiometry (TRIR) is used, where instead of a very high intensity flash pulse of light, a steady step-source of heat is used to quantitatively obtain similar information to above. The advantage of this method is that a moderate intensity light source may be sufficient. Two exemplary but not limiting embodiments of heat source 14 are depicted in FIGS. 2 and 3.

Once the surface 20 is heated, a thermal pulse or multiple thermal pulses propagate into the object. The surface temperature can then be monitored by emitted infrared radiation (numeral 22) from the surface 20 using an IR camera/recording system 24.

Thus the recording system or camera 24 is configured to collect the emitted radiation 22 that includes data representative of the propagation and evolution of the thermal pulses in the object 12. In one example, a high speed infrared (IR) focal plane array camera is used as the recording system or camera 24 for monitoring and imaging the temperature or thermal profile in the object 12. It may be noted that the IR camera, in one example, captures the thermal or temperature profiles on the same side of the object 12 as the application of heat by the heat source 14. In another exemplary embodiment (not shown), the focal plane array camera 24 may be disposed behind the object 12 on an opposite side of the heat source 14. The IR camera as described herein may be a computer-controlled, high-speed FLIR Phoenix MWIR DAS camera system. In a specific embodiment the IR camera has a cooled focal plane array (FPA) that operates in a snapshot mode in which the IR photons are accumulated at the same time by each detector of the array. The digital readout of the FPA occurs at an overall rate of 40 Mpixels/sec. Once the desired sequences of images are accumulated in memory, the temporal dependencies of the temperature at each pixel are analyzed and time of flight (tof) maps are generated as described herein below.

The system 10 also includes an image acquisition system 26 for communicating with the recording system and camera 24 and the heat source 14 via communication links 28 and 30 respectively. In another example, the image acquisition system 26 is included within the recording system/camera 24. Acquisition of thermal data is preferably initiated at the time of activating the heat source 14 either by optical triggering or by other suitable means. Activating the heat source 14 may be controlled via conventional electronics incorporated within the image acquisition system 26 or done independently, and managed by conventional video frame acquisition software running on a system computer or a processor embodied as a time of flight analysis system 32.

The time of flight analysis system 32 is configured for capturing data represented generally by the reference numeral 34 corresponding to the images from the image acquisition system 26. The time of flight analysis system 32 is used for analyzing the data, and determining lateral diffusivity and porosity values and for determining flaws using these values. According to the exemplary embodiments, time of flight analysis system 32 uses the lateral heat flow in the object 12 to determine thermal diffusivity and porosity, without thickness information. The time of flight analysis system also need not use any curve fitting to the temperature profile and is based on the creation of thermal time of flight (tof) images, shown generally as 33.

According to particular embodiments, the time of flight analysis system 32 also normalizes temperature variability in the time-temperature responses (t-T curves) while processing the time-dependence of the temperature field of the images. In more particular embodiments, the time of flight analysis system 32 is further configured to use an inflection point in time of the time-temperature responses at each pixel to determine diffusivity values corresponding to different points in the object 12.

The system 10 may also include a display monitor 36 to receive an output 38 from the time of flight analysis system 32. The display monitor may be connected to a printer or any other device for displaying the output from the time of flight analysis system 32.

FIG. 2 illustrates a diagrammatic representation of an exemplary heat source configuration, depicted generally by reference numeral 40. In this specific but non-limiting example, the heat source is a flash-pulse source, for example linear flash lamp 42 configured for applying high intensity light pulses for heating a stripe 46 of finite width on a surface of the object 12. In a specific example, four 9.6 kilo Joule (kJ) Speedotron 105 flash lamps were used.

A quench pulse controlled shutter 44 with stripe source pattern may be used in some embodiments to create a stripe 46 on the surface of the object 12. The backside (not shown) of the shutter 44, in one non-limiting example, is coated with a thin insulating Teflon layer, and the shutter is brought in direct contact with the front surface of the object to ensure that a sharp stripe edge is formed. The light from the flash lamps is thus absorbed in a very thin stripe-shaped layer on the surface of the object 12, thereby producing the desired front surface instantaneous heat source. In one example, the quenched pulse duration of the flash lamp was 2.5 ms (millisecond). The quench pulse was also used to trigger a solenoid (not shown) to retract the shutter after the flash.

Referring again to FIG. 2, a focal-plane array camera 48, for example an infrared (IR) camera may be placed in the center with flash lamps arranged around it on a ring support. During the flash, the shutter 44 is in place over the object surface creating an instantaneous stripe heat source. The shutter may be controlled by a solenoid (not shown) and in a specific embodiment it is activated such that at the end of the flash pulse it is retracted or swung out of the way so the IR camera has full view of the surface of the object. In another embodiment, traditional single-sided or reflection IR thermography measurements can be carried by removing the shutter. In addition, the flash lamps shown in FIG. 2 can be disabled and another flash lamp can be placed behind the sample for through-transmission IR thermography.

FIG. 3 illustrates a diagrammatic representation of another embodiment depicted generally by reference numeral 50, showing yet another heat source configuration. As depicted, a steady source of light is projected to continuously heat a long, uniform stripe on the surface of an object 12 by a step-heat source 52. The projected step-heat sources have additional advantage of flexibility of projecting various source patterns on the surface of the object to create and manipulate the lateral flow of heat. The step-heat source may be a slide projector, a liquid crystal display (LCD) projector, or an overhead projector. A mask 54 may be additionally used to create a patterned stripe on the surface of the object 12.

Figure 4:
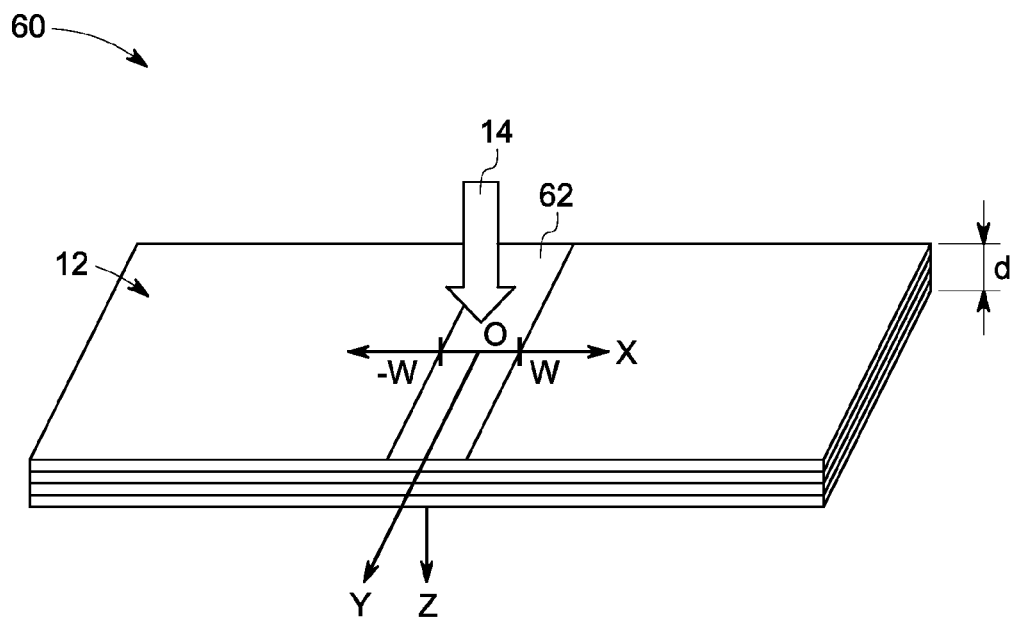
FIG. 4 is a diagrammatic representation of a stripe generated by applying a heat source on the surface of the object.

FIG. 4 is a diagrammatic representation shown generally by reference numeral 60 of a stripe 62 generated by applying a heat source 14 on the surface 20 of object 12. The object 12 in one non-limiting example is a thermally anisotropic plate of thickness d and the heat source 14 is a flash-pulse source. The long stripe 62 is created on the front surface (z=0) and has a width of 2w. The stripe is aligned with the principal diffusivity axes of the plate (x- and y-axes). The back surface is at z=d. A delta-function stripe heat source is considered. It is assumed that the plate surfaces are insulated (i.e., convection and radiation heat losses are ignored). The anisotropic material has in-plane diffusivity $\alpha_p$ in the direction perpendicular to the stripe heat source edge (x-direction), and through-plate (z-direction) diffusivity $\alpha_t$. For simplicity, the plate is assumed to extend infinitely along the x- and y-directions; the stripe 62 is assumed to extend to infinity along y-direction. Therefore the two-dimensional diffusion equation for temperature T(x,z,t) [Equation (1)]:

$$\alpha_p \frac{\partial^2 T}{\partial x^2} + \alpha_t \frac{\partial^2 T}{\partial z^2} = \frac{\partial T}{\partial t}. \tag{1}$$

The solution of Equation (1) with independent insulating boundary conditions can be expressed as a product of the solutions of two one-dimensional problems, namely, the problem of an infinite solid with instantaneous plane source, $$\alpha_p \frac{\partial^2 T}{\partial x^2} = \frac{\partial T}{\partial t}, \tag{2}$$

and the problem of a solid bounded by two parallel planes with an instantaneous plane source at one of the boundaries, $$\alpha_t \frac{\partial^2 T}{\partial z^2} = \frac{\partial T}{\partial t} \tag{3}$$

The solution of Equation (2) for the flash-pulse heat source can then be expressed as $$T(x, t) = \tag{4}$$

$$\frac{1}{2\sqrt{\pi \alpha_p t}} \int_{-w}^{w} e^{-\frac{(x-x')^2}{4\alpha_p t}} dx' = \frac{1}{2}\left[\text{erf}\left(\frac{w-x}{2\sqrt{\alpha_p t}}\right) + \text{erf}\left(\frac{w+x}{2\sqrt{\alpha_p t}}\right)\right]$$

For the case of an instantaneous plane source at z=0, the solution to Equation (3) at the front surface (z=0) can be written in the following equivalent forms:

$$T(z=0, t) = \frac{1}{d}\left[1 + 2\sum_{n=1}^{\infty} e^{-\frac{\alpha_t n^2 \pi^2 t}{d^2}}\right] \tag{5a}$$

$$T(z=0, t) = \frac{\sum_{n=-\infty}^{\infty} e^{-\frac{n^2 d^2}{\alpha_t t}}}{2\sqrt{\pi \alpha_t t}} \tag{5b}$$

The latter is obtained by the method of images and converges faster and is easier to use also for the step function heating embodiment described in FIG. 3.

Thus, T(x, z=0, t) is obtained by multiplying Equations (4) and (5b):

$$T(x, z=0, t) = \frac{1}{2}\left[\text{erf}\left(\frac{w-x}{2\sqrt{\alpha_p t}}\right) + \text{erf}\left(\frac{w+x}{2\sqrt{\alpha_p t}}\right)\right] \cdot \frac{\sum_{n=-\infty}^{\infty} e^{-\frac{n^2 d^2}{\alpha_t t}}}{2\sqrt{\pi \alpha_t t}} \tag{6}$$

The T-t curves are obtained from the thermal time of flight analysis system as explained in reference to FIG. 1 and T(x, z=0, t) is computed using Equation (6). Time of flight (tof) can then be determined by taking a time derivative of T-t and locating the inflection point.

The solution to Equation (1) for the step-function stripe heat source can be obtained by integrating Equation (6):

$$T_s(x, z=0, t) = \tag{7}$$

$$\int_0^t \frac{dt'}{4\sqrt{\pi \alpha_t (t-t')}} \left[\text{erf}\left(\frac{w-x}{2\sqrt{\alpha_p (t-t')}}\right) + \text{erf}\left(\frac{w+x}{2\sqrt{\alpha_p (t-t')}}\right)\right] \cdot \sum_{n=-\infty}^{\infty} e^{-\frac{n^2 d^2}{\alpha_t (t-t')}}.$$

It is possible to analytically solve Equation (1) for two practical exemplary situations encountered for embodiment as shown in FIG. 3, namely, the case of a stripe step function heat source on an infinitesimally thin plate and the case of a line step-function heat source on a plate of finite thickness. In the later case, for a step line heat source at x=x₀, the solution is simply written as $$T_s(x, z=0, t) = \int_0^t \frac{dt'}{2\sqrt{\pi\alpha_p(t-t')}} e^{-\frac{(x-x_0)^2}{4\alpha_p(t-t')}} \cdot \frac{\sum_{n=-\infty}^{\infty} e^{-\frac{n^2 d^2}{\alpha_t(t-t')}}}{2\sqrt{\pi\alpha_t(t-t')}}, \quad (8)$$

and yields, $$T_s(x, z=0, t) = \frac{-1}{4\pi\sqrt{\alpha_p\alpha_t}} \sum_{n=-\infty}^{\infty} Ei\left[-\frac{(x-x_0)^2}{4\alpha_p t} - \frac{n^2 d^2}{\alpha_t t}\right].$$

In principle it is possible to obtain a solution for a step-function stripe heat source on a plate of finite thickness by integrating Equation (8) from −w to w over x₀. On the other hand, for the case of a step-function stripe heat source on an infinitesimally thin plate, the solution is obtained by integrating Equation (4) over the time variable from 0 to t:

$$T_s(x, t) = \frac{t}{2}\left[\begin{array}{c} \text{erf}\frac{w-x}{2\sqrt{\alpha_p t}} + \text{erf}\frac{w+x}{2\sqrt{\alpha_p t}} + \frac{(w-x)^2}{2\alpha_p t} \cdot \text{erfc}\frac{x-w}{2\sqrt{\alpha_p t}} - \\ \frac{(w+x)^2}{2\alpha_p t} \cdot \text{erfc}\frac{x+w}{2\sqrt{\alpha_p t}} + \frac{w-x}{\sqrt{\pi\alpha_p t}} e^{-\frac{(w-x)^2}{4\alpha_p t}} + \\ \frac{w+x}{\sqrt{\pi\alpha_p t}} e^{-\frac{(w+x)^2}{4\alpha_p t}} \end{array}\right] \quad (9)$$

Equation (8) represents a practical case where the width of the stripe source is much smaller than the thickness of the plate, while Equation (9) represents the case of a very thin plate and a wide stripe source.

Figure 5:
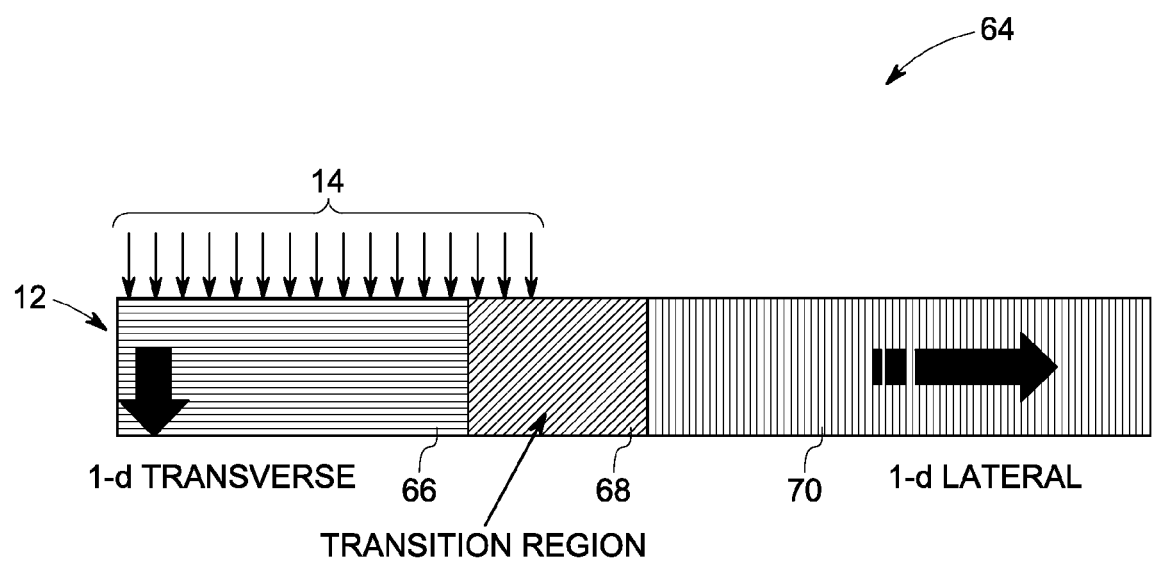
FIG. 5 is a diagrammatic representation illustrating the physics of lateral heat flow.

FIG. 5 illustrates the physics of the lateral heat flow. As illustrated in FIG. 5, just across the heat source 14, the heat flow is mainly through the plate thickness (1-d transverse), shown generally by reference numeral 66 and is governed by equation (5) as described herein above. As the heat flows towards the edge of the source (or stripe), there is a mixed heat flow with transition from 1-d transverse to 1-d lateral heat flow, this is shown as transition region 68. Away from the heat edge, and once the plate has thermalized, only 1-d lateral heat flow is possible and is shown by reference numeral 70. The lateral heat flow as shown here is governed by equation (4) described herein above.

Figure 6:
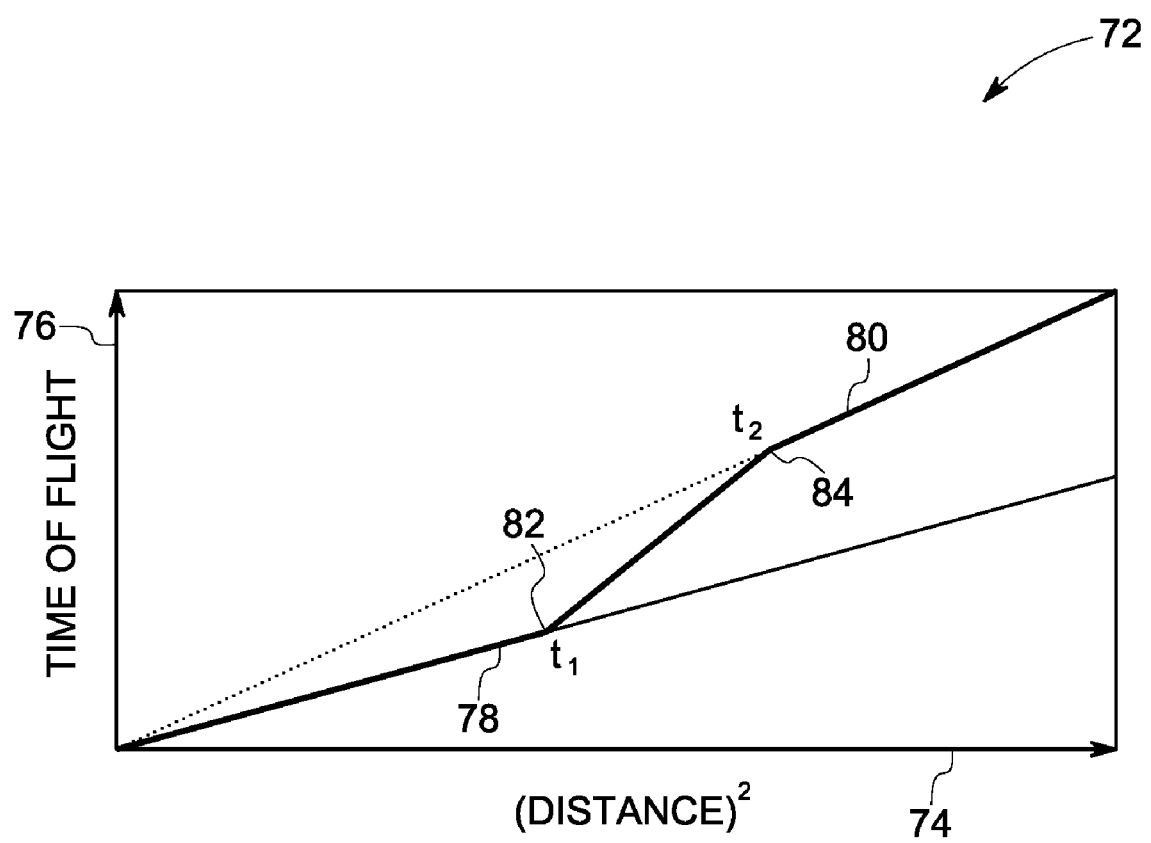
FIG. 6 is a diagrammatic representation of exemplary time of flight (tof) curves obtained by using a thermal time of flight analysis system.

The physics as described in FIG. 5 can be correlated to the exemplary tof curves as shown in FIG. 6. FIG. 6 is a diagrammatic representation of the tof curves 72 obtained from time of flight analysis system of FIG. 1. The X-axis is denoted generally by reference numeral 74 and indicates the square of the distance from heat source edge and Y-axis is denoted generally by reference numeral 76 and indicates the time of flight. The time of flight analysis described herein includes using an inflection point on the T-t (temperature-time) curve obtained from the image acquisition system described in reference with FIG. 1, for analyzing the data from both transmission mode imaging technique and reflection mode imaging technique. The "inflection point" is defined as a point in time where the time-temperature curve has the highest slope. The time corresponding to inflection point is denoted as an "effective time of flight" (tof) and denotes the time of travel of thermal pulses. The time of flight curve comprises at least three regions, where a first one of the regions has a slope 1, wherein a third one of the regions has a slope two, and wherein an intermediate one of the regions is bounded by a first and a second time point $t_1$ and $t_2$. Slope 1 indicated by reference numeral 78 and slope 2 indicated by reference numeral 80 give lateral (in-plane) diffusivity $\alpha_p$, while t1 indicated by reference numeral 82 and $t_2$ indicated by reference numeral 84 relate to through-plate diffusivity $\alpha_t$. The expressions for t1, t2 and slope 1 and slope 2 are given below:

$$t_1 = \frac{1.5 d^2}{\pi^2 \alpha_t} \quad (10)$$

$$\text{Slope } 1 = \frac{1}{\pi^2 \alpha_p} \quad (11)$$

$$t_2 = \frac{4 d^2}{\pi^2 \alpha_t} \quad (12)$$

$$\text{Slope } 2 = \frac{1}{6\alpha_p} \quad (13)$$

where "d" is the thickness of the stripe.

Initially, heat flows in the plate along both the x- and z-directions, but after $t_2$, heat flows mostly along x-direction. It leads to the conclusion that since the plate has not fully thermalized until $t_2$ as shown in FIG. 4, the in-plane diffusivity $\alpha_p$ in slope 1 is mainly due to the surface layers, while the $\alpha_p$ in slope 2 is the effective diffusivity of the full plate in the limit of one-dimensional lateral heat flow. Thus in an exemplary embodiment where the article comprises multiple layers that include multiple surface layers, the thermal diffusivity of the surface layers is determined from Slope 1. In another exemplary embodiment for an article of thickness d a through-thickness thermal diffusivity $\alpha_t$ is determined by using an equation for the time $t_1$.

Moreover, $t_2$ represents full thermalization and can be used to calculate $\alpha_t$ if d (thickness, as shown in FIG. 4) is known. For isotropic materials where $\alpha_p = \alpha_t$, $t_2$ can be used to independently determine d or thickness of the object.

It is specifically advantageous to use time of flight analysis since no calibration is necessary in order to obtain the diffusivity value. The images are more robust since dependence on temperature has been eliminated. The time of flight analysis is rapid since only an inflection point is required on the T-t curve. The results, thus obtained using time of flight analysis are independent of the complex shape of a component since time of flight analysis depends on time, not temperature.

Thus the thermal diffusivity calculation using time of flight analysis does not require use of any standard reference (or calibration), and therefore thermal diffusivity in the object at any point on the surface of the object can be reliably evaluated.

Thus the lateral heat flow method in conjunction with time of flight analysis outlined in FIG. 6 and equations (10)-(13) can advantageously be used to quantify porosity from a single-sided measurement that does not require knowledge of local thickness of the structure, and therefore eliminates any need for two-sided access of the object. This method permits the independent determination of both the thermal diffusivity and thickness in isotropic materials. In anisotropic materials, the in-plane diffusivity can be obtained independently of thickness using this method, however, the transverse component still requires thickness information. Another advantage of the techniques described herein is that they do not require any sort of time consuming, iterative process of curve fitting to the full time-temperature (T-t) data to extract diffusivity values. Further, since the techniques are based on the determination of time of flight, they are unaffected by the surface emissivity variations or reflections. Further, as discussed herein above, determination of diffusivity from slope 1 in FIG. 6, provides a means of determining diffusivity of the first few surface layers of a very thick structure. These layers are very important for the structural integrity. In general, conventional IR methods have difficulties in measuring very thick composites due to inadequacy of amount of heat that can be supplied and very long heat travel times encountered in such materials. Further, besides diffusivity, other properties of the composite articles or material, such as porosity, can also be obtained from the measured in-plane diffusivity. Presence of porosity in the material impedes heat flow. Thus the more the porosity, the smaller the thermal diffusivity and the two can be either empirically related using measurements based on porosity standards or from physics based first principles calculations, such as in Ringermacher et al. ("Discriminating Porosity in Composites using Thermal Depth Imaging," Review of Quantitative Nondestructive Evaluation Vol. 21, Ed. D. O. Thompson and D. E. Chimenti, 2002 AIP). The porosity of structural composite materials is an important parameter that is a possible predictor of the integrity and strength of a structure made using these composites, and therefore it is a very critical quantity to measure. Thus the porosity estimation based on data obtained from the above techniques does not require thickness information.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for determining porosity of an article, the method comprising:
    heating a surface of the article;
    capturing image data corresponding to an evolution of lateral heat flow from the surface of the article;
    applying a thermal time of flight analysis on the image data; and
    determining thermal diffusivity and porosity values of the article using the thermal time of flight analysis for the lateral heat flow.

2. The method of claim 1, wherein the thermal time of flight analysis comprises generating a curve for the time of flight as a function of a distance from a heat source edge, wherein the curve comprises at least three regions, wherein a first one of the regions has a slope 1, wherein a third one of the regions has a slope 2, and wherein an intermediate one of the regions is bounded by a first and a second time point $t_1$ and $t_2$, and
    wherein the thermal diffusivity is calculated from the slopes 1 and 2 and the time points $t_1$ and $t_2$.

3. The method of claim 2, wherein determining the thermal diffusivity comprises determining an in-plane thermal diffusivity $\alpha_p$ using an equation for the slope 1:

$$\text{Slope 1} = \frac{1}{\pi^2 \alpha_p}.$$

4. The method of claim 2, wherein determining the thermal diffusivity comprises determining an in-plane thermal diffusivity $\alpha_p$ using an equation for the slope 2:

$$\text{Slope 2} = \frac{1}{6\alpha_p}.$$

5. The method of claim 2, wherein the article comprises a plurality of layers including a plurality of surface layers, the method further comprising determining a thermal diffusivity $\alpha_p$ of the surface layers using an equation:

$$\text{Slope 1} = \frac{1}{\pi^2 \alpha_p}.$$

6. The method of claim 2, wherein the article comprises an isotropic material, the method further comprising determining a thermal diffusivity $\alpha$ of the article using an equation:

$$\text{Slope 1} = \frac{1}{\pi^2 \alpha}.$$

7. The method of claim 2, wherein determining the thermal diffusivity of the article of thickness d comprises determining a through-thickness thermal diffusivity $\alpha_t$ using an equation for the time $t_1$:

$$t_1 = \frac{1.5d^2}{\pi^2 \alpha_t}.$$

8. The method of claim 2, wherein determining the thermal diffusivity comprises determining a through-thickness thermal diffusivity $\alpha_t$ using an equation for the time $t_2$:

$$t_2 = \frac{4d^2}{\pi^2 \alpha_t}$$

wherein d is the thickness of the article.

9. The method of claim 2, wherein the article comprises an isotropic material characterized by a thermal diffusivity $\alpha$, the method further comprising independently determining both thermal diffusivity, $\alpha$, and thickness d of the article by using equations, $$t_1 = \frac{1.5d^2}{\pi^2 \alpha} \text{ or } t_2 = \frac{4d^2}{\pi^2 \alpha},$$

and $$\text{Slope 1} = \frac{1}{\pi^2 \alpha} \text{ or } \text{Slope 2} = \frac{1}{6\alpha}.$$

10. The method of claim 1 further comprising spatially modulating the heating using a shutter.

11. The method of claim 1 further comprising spatially modulating the heating using a mask to create a pattern on the surface of the composite article.

12. The method of claim 1, wherein the heating comprises applying one or more flash-pulses.

13. The method of claim 1, wherein the heating is performed using a step-heat source.

14. The method of claim 1, wherein the porosity values are determined using the thermal diffusivity values.

15. A non-destructive evaluation system for inspecting an object, the system comprising:
- a heat source configured for heating a surface of the object;
- a focal plane array camera configured to capture a plurality of images corresponding to an evolution of lateral heat flow from the surface;
- an image acquisition system configured for capturing data corresponding to the plurality of images from the focal plane array camera; and
- a time of flight analysis system configured to perform a thermal time of flight analysis on the data, and determine diffusivity and porosity values using the thermal time of flight analysis for the lateral heat flow in the object.

16. The system of claim 15, wherein the heat source comprises a flash-pulse source.

17. The system of claim 16 further comprising a shutter configured to create a stripe of finite width on the surface of the object.

18. The system of claim 15, wherein the heat source comprises a step-heat source.

19. The system of claim 18 further comprising a mask configured to create a pattern on the surface of the object.

20. The system of claim 15, wherein the focal plane array camera is configured to capture a plurality of images from one side of the object.

21. The system of claim 15, wherein the plurality of images comprise temperature-time responses at plurality of points in the object.

* * * * *

UNITED STATES PATENT AND TRADEMARK OFFICE
CERTIFICATE OF CORRECTION

PATENT NO. : 7,549,789 B2
APPLICATION NO. : 11/765470
DATED : June 23, 2009
INVENTOR(S) : Tralshawala et al.

It is certified that error appears in the above-identified patent and that said Letters Patent is hereby corrected as shown below:

In Column 6, Lines 20-25, in Equation "5(a)", delete "$\frac{1}{d}\left[1 + 2\sum_{n=1}^{\infty} e^{\frac{\alpha_t n^2 \pi^2 t}{d^2}}\right]$"

and insert -- $\frac{1}{d}\left[1 + 2\sum_{n=1}^{\infty} e^{-\frac{\alpha_t n^2 \pi^2 t}{d^2}}\right]$ --, therefor.

In Column 6, Line 64, delete "Equation (1)" and insert --Equation (7)--, therefor.

Signed and Sealed this

Thirteenth Day of April, 2010

David J. Kappos
*Director of the United States Patent and Trademark Office*